United States Patent [19]

Römisch et al.

[11] Patent Number: 5,136,026

[45] Date of Patent: Aug. 4, 1992

[54] PROCESS FOR REMOVING TOXINS FROM PROTEIN SOLUTIONS

[75] Inventors: Jürgen Römisch; Norbert Heimburger, both of Marburg, Fed. Rep. of Germany

[73] Assignee: Behringwerke Aktiengesellschaft, Marburg, Fed. Rep. of Germany

[21] Appl. No.: 683,524

[22] Filed: Apr. 9, 1991

Related U.S. Application Data

[63] Continuation of Ser. No. 505,609, Apr. 6, 1990, abandoned.

[30] Foreign Application Priority Data

Apr. 10, 1989 [DE] Fed. Rep. of Germany ....... 3911629

[51] Int. Cl.⁵ ............................ C07K 3/22; C07K 3/28
[52] U.S. Cl. ................................. 530/416; 530/380; 530/394; 530/395; 530/412
[58] Field of Search ............... 530/380, 394, 395, 412, 530/416

[56] References Cited

U.S. PATENT DOCUMENTS 4,372,888  2/1983  Hjelmeland .................. 540/110
4,990,597  2/1991  Lobermann .................. 530/392

OTHER PUBLICATIONS

Randall-Hazelbauer et al., J. Bacteriology, vol. 116(3) pp. 1436–1446 (1973).
Biochem. 8(10):4063–67 (Oct. 1969), McIntire et al., "Studies on a Lipopolysaccharide from *Escherichia coli*. Heterogeneity and Mechanism of Reversible Inactivation by Sodium Deoxycholate".
Biochem. 18(20):4425–30 (1979), Schwindler et al., "Interaction of Divalent Cations and Polymyxin B with Lipopolysaccharide".

*Primary Examiner*—Merrell C. Cashion, Jr.
*Assistant Examiner*—Andrew G. Rozycki
*Attorney, Agent, or Firm*—Finnegan, Henderson, Farabow, Garrett and Dunner

[57] ABSTRACT

A process for removing toxins from solutions of proteins, in which an aqueous solution of a protein which contains a buffer substance, a chelating agent and a detergent is subjected to an ion exchange chromatography, is described.

9 Claims, No Drawings

PROCESS FOR REMOVING TOXINS FROM PROTEIN SOLUTIONS

This application is a continuation, of application Ser. No. 07/505,609, filed Apr. 6, 1990, now abandoned.

The invention relates to a process for removing of toxins from solutions of proteins, in particular from lipocortins PP4, PP4-X (PAP II), PAP III, p68 and lipocortins I and II.

BACKGROUND OF THE INVENTION

Placental tissue protein PP4, proteins PP4-X, PAP III and p68, as well as lipocortins I and II, display homology in the amino acid sequences and belong to a family of proteins called lipocortins.

These proteins have antiinflammatory and anticoagulant effects. They have been detected in many organs and can be isolated from the latter.

Preparation from tissues, for example from human placenta, or of proteins prepared by gene manipulation, for example expressed in E. coli, such as rPP4 or rPP4-X, is associated with isolation, together with these proteins, of substances which are toxic for humans, such as bacterial lipopolysaccharides. Despite high purity (greater than 95% based on the protein content), the isolated proteins showed heavy contamination with toxic substances in toxicity tests such as the Limulus test or after administration of therapeutic doses (1 mg of protein/kg of body weight) to rabbits.

It was not possible to remove these evidently protein-associated contaminants either by chromatographic processes or filtration techniques such as sterile filtration or by the use of non-ionic detergents or of chelating reagents, alone or in combination.

Hence the object of the invention was to develop processes for removing toxins deriving from organs, tissues and cell cultures in proteins of the lipocortin family which have been isolated as well as prepared by gene manipulation, which do not impair the biological activity of the proteins and thus permit potential use as therapeutics for coagulation and/or inflammatory disorders.

It has been found, surprisingly, that toxic substances can be removed from these proteins by ion exchange chromatography in the presence of chelating reagents in combination with ionic detergents, without an adverse effect on the biological activity.

SUMMARY OF THE INVENTION

Thus the invention relates to a process for removing toxins from a protein solution, which comprises subjecting a protein in an aqueous buffer solution in the presence of a chelating agent and of an ionic detergent to anion exchange chromatography.

This process is especially applicable to lipocortins, which can be of natural or biotechnological origin, especially originating from gene manipulation.

DETAILED DESCRIPTION OF THE INVENTION

Examples of chelating agents which can be used are EDTA, EGTA, a salt of citric acid or oxalic acid or a combination thereof.

Examples of ionic detergents which can be used are cholic acid, taurocholic acid, taurodehydrocholic acid, deoxycholic acid, taurodeoxycholic, acid or taurochenodeoxycholic acid or a slat thereof or a mixture thereof.

It is possible to use as ion exchanger an anion exchanger, preferably DEAE- ®Sepharose, - ®Sephacel, - ®Fractogel or Q- ®Sepharose, particularly preferably DEAE- ®Sepharose.

The chelating agent and the detergent can be removed from the protein-containing solution after the treatment according to the invention by dialysis or by chromatography in a buffer solution of pH 7.4–9.5, preferably pH 8.0–9.5, particularly preferably pH 8.0–9.0.

In one procedure, a solution of the protein which contains a buffer substance, such as tris, glycine, HEPES or PBS, with a pH of 7.0–10.0, and at least 0.1 mmol/l of a chelating reagent such as EDTA, EGTA, of a salt of citric acid or of oxalic acid or of a combination of these and at least 0.05 g/l of an ionic detergent such as Na chol., Na Doc., Na Tdoc., Na Tchol., Tcheno-Doc or Tdcho. or of a mixture of these, is brought into contact with an anion exchanger, the exchanger is washed with buffer solution, and the adsorbed protein is eluted with a salt gradient, for example using LiCl, KCl or NaCl.

In a preferred procedure, a solution of the protein with a concentration of 0.01–30 mg/ml, particularly preferably 0.2–5 mg/ml, which contains tris in a concentration of 2–80 mmol/l and a pH of 7.0–9.5, particularly preferably 20 mmol/l tris/HCl and a pH of 8.0–9.0, as well as 1–100 mmol/l of a chelating reagent, particularly preferably 5–20 mmol/l EDTA, and 0.2–5 g/l, particularly preferably 0.8–1.5 g/l, Na chol. or Na Doc. or of a mixture, is brought into contact with DEAE- ®Sepharose, - ®Sephacel, - ®Fractogel, or Q- ®Sepharose, particularly preferably DEAE- ®Sepharose. After the exchanger has been washed with buffer solution, the adsorbed protein is eluted with a linear increasing NaCl gradient.

Chelating reagents and detergents can be removed from the protein-containing column flow-throughs or eluates by dialysis against a buffer solution composed of tris, HEPES, glycine or PBS, particularly preferably against a buffer solution of pH 8.0–9.0, or by a further chromatographic step such as gel permeation chromatography with AcA 202 or AcA 54.

It is possible, where appropriate, for the preparations treated in this way to be further purified. The following abbreviations have been used for the description:

| | |
|---|---|
| DEAE: | diethylaminoethyl |
| EDTA: | ethylenediaminotetraacetic acid |
| HEPES: | N-2-hydroxyethylpiperazine-N-2-ethane-sulfonic acid |
| Na Chol: | sodium cholate |
| Na Doc: | sodium deoxycholate |
| Na Tchol: | sodium taurocholate |
| Na Tdoc: | sodium taurodeoxycholate |
| PBS: | sodium or potassium phosphate buffer |
| rPP4: | PP4 prepared by genetically engineered expression in E. coli |
| rPP4-X: | PP4-X prepared by genetically engineered expression in E. coli |
| PAP III: | placental anticoagulant protein III |
| PAGE: | polyacrylamide gel electrophoresis |
| Q: | quaternary amine |
| SDS: | sodium dodecyl sulfate |
| Tcheno-Doc: | taurochenodeoxycholic acid |
| Tdchol: | taurohydrocholic acid |
| tris: | tris(hydroxymethyl)aminomethane |

The invention is illustrated by the examples which follow:

The starting substances employed for the detoxification were preparations of the proteins PP4, PPr-X, PAP III, p68, lipocortins I and II from human placenta and of proteins rPP4 and rPP4-X from transformed *E. coli* cultures with a purity of greater than 95% based on the protein content, in a buffer solution composed of 0.02 mol/l tris/HCl, pH 8.5, with a protein concentration of 2.5 mg/ml. These preparations had an evident content of toxic substances (Table I) as was determined using the Limulus test (carried out in solutions at pH 7.2) and the animal model.

Toxicity tests

1. Limulus test

This test was carried out as described by Concept GmbH (Heidelberg, Germany): 0.1 ml of the protein-containing solution to be tested was gently mixed with 0.1 ml of Limulus amebocyte lysate in a pyrogen-free tube, and the tube was incubated at 37° C. without shaking for 60 min. After the end of the incubation time, the tube was examined visually to find whether a solid gel had formed. The pyrogenicity of the tested substance, expressed in EU (endotoxin units), was determined using a calibration plot constructed with the aid of a reference endotoxin (EC-5).

2. Pyrogen test on rabbits

The toxicity of the protein samples was determined by measuring the increase in the body temperatures (rectal) of rabbits compared with the body temperature determined in a 90-minute preliminary test. Protein samples were administered i.v. in a bolus (1 mg/kg of body weight) into an ear vein of the rabbits, and the body temperature was recorded for a period of 180 min. The highest value was used as basis for the evaluation. Samples were assessed as pyrogen-free if the total of the temperature differences of 6 animals was less than or equal to 2.2° C.

buffer, and adsorbed proteins were eluted with an NaCl gradient increasing linearly.

The eluates were extensively dialyzed against a buffer solution composed of 0.02 mol/l tris/HCl, pH 8.5, and subsequently against a buffer solution composed of 0.02 mol/l tris/HCl, pH 7.2, and the dialyzates were examined for toxicity both in the Limulus test and in the pyrogen test on rabbits. The proteins treated in this way caused only very low or no increases in temperature in the pyrogen test or scarcely measurable endotoxin contents in the Limulus test (Table I), and it was possible to assess them as pyrogen-free.

Proteins PP4-X and rPP4-X were not adsorbed onto the gel material under the said conditions and were found in the column flow-through, but they were likewise pyrogen-free after the stated process had been carried out (Table I).

The biological activity, examined using the modified prothrombin time, based on the protein concentration, was fully retained by comparison with the starting materials through this process step. The yields of the proteins were between 64 and 85% based on the toxic starting materials.

EXAMPLE 2

PP4-, rPP4-, PP4-X-, rPP4-X-, PAP III-, p68- or lipocortin I- or II-containing buffer solutions were mixed with Na Chol or Na Tchol to a final concentration of 0.5 g/l in each case, as well as 0.01 mol/l EDTA, the latter were brought into contact with Q-®Sepharose (from Pharmacia, Sweden) equilibrated with 0.02 mol/l PBS, pH 8.5, 0.01 mol/l EDTA, 0.05 g/l Na Chol and 0.5 g/l Na Tchol (column buffer) in a column, the gel material was washed, and adsorbed proteins were eluted with an NaCl gradient increasingly linearly.

The procedures for further treatment of the protein solutions and examination thereof for toxicity were as described in Example 1. The results of these investigations corresponded to those for Example 1 and are listed in Table I.

TABLE I

| | Starting material | | After detoxification | | | |
| | Toxicity test | | Toxicity test | | Coagulation | |
| Protein | Limulus EU/ml | Rabbits[1] t (°C.) | Limulus EU/ml | Rabbits t (°C.) | inhibition[2] % | Yield[3] % |
|---|---|---|---|---|---|---|
| PP4 | *250 | 6.6 | **0.25 | 0.8 | 100 | 70 |
| rPP4 | *250 | 10.8 | 2.0 | 1.4 | 100 | 65 |
| PP4-X | 50 | 4.8 | **0.25 | 1.0 | 96 | 80 |
| rPP4-X | *250 | 9.0 | 2.0 | 1.2 | 95 | 70 |
| p68 | 250 | 6.0 | 0.5 | 0.8 | 97 | 65 |
| Lipocortin I | 50 | 5.4 | 0.5 | 1.4 | 93 | 70 |
| Lipocortin II | 50 | 4.8 | 0.25 | 1.0 | 98 | 85 |
| Factor XIII | 50 | 3.6 | 50 | 3.4 | — | 80 |

*greater than
**less than
[1]temperature difference (see text); total for 6 rabbits
[2]based on the coagulation inhibition (modified thromboplastin test) by the starting materials (= 100%)
[3]based on the amount (= 100%) of extra pure proteins employed for the detoxification

EXAMPLE 1

After addition of EDTA to a final concentration of 0.01 mol/l, while checking the pH, and 0.1% Na Doc, the PP4-, rPP4-, PP4-X-, rPP4-X-, PAP III-, p68- or lipocortin I- or II-containing solutions were brought into contact with DEAE-®Sepharose (from Pharmacia, Sweden) equilibrated with 0.02 M tris/HCl, pH 8.5, 0.01 M EDTA and 0.1% Na Doc. (column buffer) in a column, the gel material was washed with column

We claim:
1. A process for removing toxins from protein solutions, which comprises subjecting an aqueous buffer solution containing lipocortin or placental proteins, a chelating agent and an ionic detergent to anion exchange chromatography.
2. The process as claimed in claim 1, wherein the protein is a lipocortin.

3. The process as claimed in claim 1, wherein EDTA, EGTA, a salt of citric acid or oxalic acid or a combination thereof is used as the chelating agent.

4. The process as claimed in claim 3, wherein the chelating agent is used in a concentration of 1-100 mmol/l.

5. The process as claimed in claim 1, wherein cholic acid, taurocholic acid, taurodehydrocholic acid, deoxycholic acid, taurodeoxycholic acid or taurochenodeoxycholic acid or a salt thereof or a mixture thereof is used as the detergent.

6. The process as claimed in claim 5, wherein the detergent is used in a concentration of 0.02-5 g/l.

7. The process as claimed in claim 5, wherein DEAE-®Sepharose, -®Sephacel, -®Fractogel or Q-®Sepharose is used as the anion exchanger.

8. The process as claimed in claim 1, wherein DEAE-®Sepharose is used as the anion exchanger.

9. The process as claimed in claim 1, wherein the chelating agent and detergent are removed from the protein-containing solution by dialysis or chromatography in a buffer solution of pH 7.5-9.5.

* * * * *